United States Patent [19]

Berger et al.

[11] Patent Number: 4,707,484
[45] Date of Patent: Nov. 17, 1987

[54] SUBSTITUTED PIPERIDINOMETHYLINDOLONE AND CYCLOPENT(B)INDOLONE DERIVATIVES

[75] Inventors: Leo Berger, Montclair; Wallace M. Dairman, Manahawkin; Thomas F. Mowles, Pine Brook; Gary L. Olson, Westfield, all of N.J.

[73] Assignee: Hoffmann-La Roche Inc., Nutley, N.J.

[21] Appl. No.: 934,756

[22] Filed: Nov. 25, 1986

[51] Int. Cl.⁴ .................. A61K 31/395; C07D 521/00
[52] U.S. Cl. ....................................... 514/278; 546/20
[58] Field of Search ........................... 546/20; 514/278

[56] References Cited

U.S. PATENT DOCUMENTS 3,467,755  9/1969  Schoen et al. ...................... 514/415
3,759,927  9/1973  Huebner ................................ 546/20

FOREIGN PATENT DOCUMENTS

67/4863  8/1967  South Africa ...................... 514/415

Primary Examiner—Robert T. Bond
Attorney, Agent, or Firm—Jon S. Saxe; Bernard S. Leon; Matthew Boxer

[57] ABSTRACT

Compounds of the formula

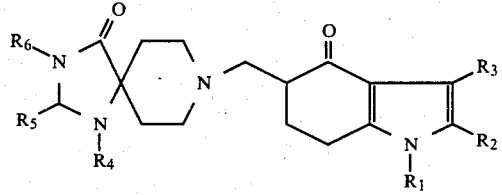

wherein $R_1$ is hydrogen, lower alkyl or acyl; $R_2$ and $R_3$ independently are lower alkyl, aralkyl or alkenyl or $R_2$ and $R_3$ together form a ring of 5 to 8 carbon atoms; $R_4$ is phenyl, substituted phenyl, cyclohexyl, substituted cyclohexyl, cyclopentyl, substituted cyclopentyl, cycloheptyl, or substituted cycloheptyl; $R_5$ is hydrogen or lower alkyl; $R_6$ is hydrogen, lower alkyl or acyl; and pharmaceutically acceptable acid addition salts thereof are described. The compounds of formula I and pharmaceutically acceptable acid addition salts thereof are anti-emetic agents which lack central nervous system side effects.

12 Claims, No Drawings

SUBSTITUTED PIPERIDINOMETHYLINDOLONE AND CYCLOPENT(B)INDOLONE DERIVATIVES

BRIEF SUMMARY OF THE INVENTION

The invention relates to compounds of the formula

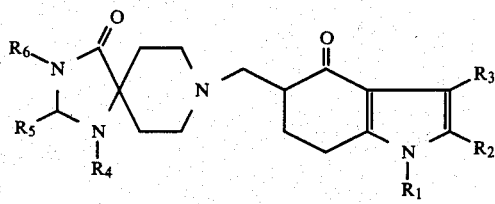

wherein $R_1$ is hydrogen, lower alkyl or acyl; $R_2$ and $R_3$ independently are lower alkyl, aralkyl, or alkenyl, or $R_2$ and $R_3$ together form a ring of 5 to 8 carbon atoms; $R_4$ is phenyl, substituted phenyl, cyclohexyl, substituted cyclohexyl, cyclopentyl, substituted cyclopentyl, cycloheptyl, and substituted cycloheptyl; $R_5$ is hydrogen or lower alkyl; and $R_6$ is hydrogen, lower alkyl or acyl; and pharmaceutically acceptable acid addition salts thereof. The compounds of formula I are useful as antiemetic agents.

DETAILED DESCRIPTION OF THE INVENTION

As used herein, the term "lower alkyl", denotes any straight or branched chain saturated hydrocarbon containing 1 to 7 carbon atoms, for example, methyl, ethyl, propyl, isopropyl, butyl, t-butyl, neopentyl, pentyl, heptyl and the like. The term "alkenyl" denotes a straight or branched chain unsaturated hydrocarbon containing 2 to 7 carbon atoms, for example, vinyl, allyl and the like. The term "aralkyl" denotes an alkyl substituted by an aryl, for example phenylethyl, or more preferably, benzyl. The term "aryl" denotes phenyl or phenyl bearing one or more substituents selected from the group consisting of halogen, trifluoromethyl, lower alkyl, lower alkoxy, nitro, amino, lower alkylamino and di-lower alkylamino. The term "lower alkoxy" denotes an alkyl ether group in which the lower alkyl group is as described above, for example, methoxy, ethoxy, propoxy, pentoxy, and the like. The term "acyl" denotes an "alkanoyl" group derived from an aliphatic carboxylic acid of 1 to 7 carbon atoms, for example, formyl, acetyl, propionyl and the like. The term "halogen" denotes all the halogens, that is, bromine, chlorine, fluorine, and iodine. The term "lower alcohol" denotes alcohols of 1 to 4 carbon atoms such as methanol, ethanol, propanol, and butanol.

As used herein the term "substituted" denotes substituted by one or more substituents selected from chlorine, fluorine, bromine, iodine, hydroxy, or lower alkyl.

The invention relates to compounds of the formula

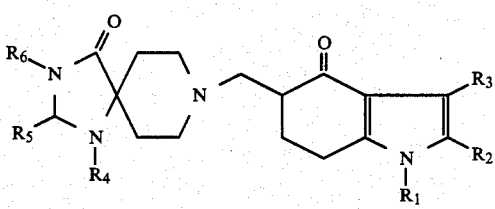

wherein $R_1$ is hydrogen, lower alkyl or acyl; $R_2$ and $R_3$ independently are lower alkyl, aralkyl or alkenyl, or $R_2$ and $R_3$ together form a ring of 5 to 8 carbon atoms; $R_4$ is phenyl, substituted phenyl, cyclohexyl, substituted cyclohexyl, cyclopentyl, substituted cyclopentyl, cycloheptyl, and substituted cycloheptyl; $R_5$ is hydrogen or lower alkyl; $R_6$ is hydrogen; lower alkyl or acyl; and pharmaceutically acceptable salts thereof.

A preferred group of compounds of formula I are those wherein $R_5$ and $R_6$ are each hydrogen.

An especially preferred group of compounds of formula I are those wherein $R_5$ and $R_6$ are each hydrogen and $R_2$ and $R_3$ together form a 5 carbon ring; and $R_4$ is phenyl.

Preferred compounds of formula I are:
8-[(3-ethyl-4,5,6,7-tetrahydro-2-methyl-4-oxo-1-H-indol-5-yl)methyl]-1-phenyl-1,3,8-triazaspiro[4.5]-decan-4-one; and
8-[4,5,6,7-tetrahydro-(2,3-dimethyl-4-oxo-1H-indol-5-yl)methyl]-1-phenyl-1,3,8-triazaspiro[4.5]decan-4-one.

A most preferred compound of formula I is:
1,2,3,5,6,7-hexahydro-7-[(4-oxo-1-phenyl-1,3,8-triazaspiro[4.5]decan-8-yl)methyl[-4H-cyclopent[b]indol-8(8H)-one.

Exemplary of the compounds of formula I are:
1,2,3,5,6,7-hexahydro-7-[(4-oxo-1-cycloheptyl-1,3,8-triazaspiro[4.5]decan-8-yl)methyl]-4H-cyclopent[b]indol-8(8H)-one;
1,2,3,5,6,7-hexahydro-7-[(4-oxo-1-butyl-1,3,8-triazaspiro[4.5]decan-8-yl)methyl]-4H-cyclopent[b]indol-8(8H)-one;
1,2,3,5,6,7-hexahydro-7-[(4-oxo-1-methyl-1,3,8-triazaspiro[4.5]decan-8-yl)methyl]-4H-cyclopent[b]indol-8(8H)-one;
1,2,3,5,6,7-hexahydro-7[(4-oxo-1-(4-chlorophenyl)-1,3,8-triazaspiro[4.5]decan-8-yl)methyl]-4H-cyclopent[b]indol-8(8H)-one;
1,2,3,5,6,7-hexahydro-7-[(4-oxo-1-(4-methylphenyl)-1,3,8-triazaspiro[4.5]decan-8-yl)methyl]-4H-cyclopent[b]indol-8(8H)-one;
1,2,3,5,6,7-hexahydro-7-[(4-oxo-1-phenyl-1,3,8-triazaspiro[4.5]decan-8-yl)methyl]-4-methyl-4H-cyclopent[b]indol-8(8H)-one;
1,2,3,5,6,7-hexahydro-7-[(4-oxo-1-phenyl-1,3,8-triazaspiro[4.5]decan-8-yl)methyl]-4-acetyl-4H-cyclopent[b]indol-8(8H)-one;
8-[(3-ethyl-4,5,6,7-tetrahydro-2-(1-propenyl)-4-oxo-1H-indol-5-yl)methyl]-1-phenyl-1,3,8-triazaspiro[4.5]decan-4-one;
8-[(3-ethyl-4,5,6,7-tetrahydro-2-(1-phenylmethyl)-4-oxo-1H-indol-5-yl)methyl]-1-phenyl-1,3,8-triazaspiro[4.5]decan-4-one;
8-[(3-ethyl-4,5,6,7-tetrahydro-2-methyl-4-oxo-1H-indol-5-yl)methyl]-1-(4-methylcyclohexyl)-1,3,8-triazaspiro[4.5]decan-4-one;
8-[(3-ethyl-4,5,6,7-tetrahydro-2-methyl-4-oxo-1H-indol-5-yl)methyl]-1-phenyl-3-methyl-1,3,8-triazaspiro[4.5]decan-4-one;
8-[(1,2,3,4,5,6,7,8-octahydro-8-oxocyclopent[b]indol-7-yl)methyl]-2-methyl-1-phenyl-1,3,8-triazaspiro[4.5]decan-4-one;
8-[(1,2,3,4,5,6,7,8-octahydro-8-oxocyclopent[b]indol-7-yl)methyl]-1-cyclohexyl-1,3,8-triazaspiro[4.5]decan-4-one;
8-[(3-ethyl-4,5,6,7-tetrahydro-2-methyl-4-oxo-1H-indol-5-yl)methyl]-1-cyclohexyl-1,3,8-triazaspiro[4.5]decan-4-one;

8-[4,5,6,7-tetrahydro-(2,3-dimethyl-4-oxo-1H-indol-5-yl)methyl]-1-butyl-1,3,8-triazaspiro[4.5]decan-4-one;

8-[4,5,6,7-tetrahydro-(2,3-dimethyl-4-oxo-1H-indol-5-yl)methyl]-1-cyclopentyl-1,3,8-triazaspiro[4.5]decan-4-one;

8-[4,5,6,7-tetrahydro-(2,3-dimethyl-4-oxo-1H-indol-5-yl)methyl]-1-(2-methylcyclopentyl)-1,3,8-triazaspiro[4.5]decan-4-one; and 8-[2,3,4,5,6,7,8,9-octahydro-4-oxo-1H-carbazol-3-yl)methyl]-1-phenyl-1,3,8-triazaspiro[4.5]decan-4-one.

In accordance with the invention, the compounds of formula I can be prepared as set forth in Formula Scheme I below.

Formula Scheme I

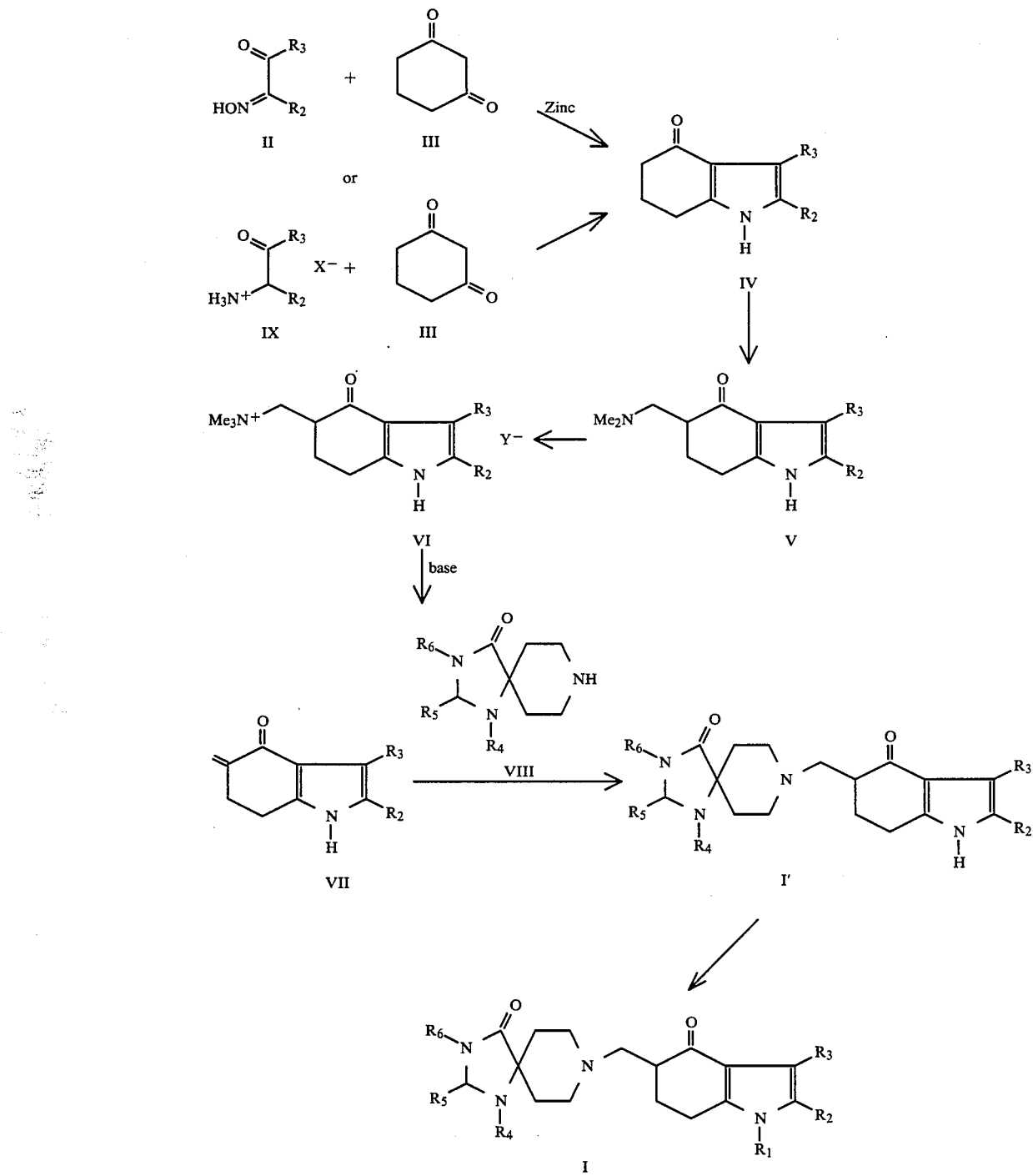

In Formula Scheme I, the reaction of an oxime compound of formula II which is a known compound or can be prepared in accordance with known methods, with the diketone of formula III, which is a known compound, is carried out under conditions typical of the Knorr reaction. These conditions include using a solvent such as 50 to 100% aqueous acetic acid which may optionally contain a cosolvent such as a lower alkanol like methanol. The reducing agent in this Knorr pyrrole synthesis is zinc dust employed in at least a stoichiometric amount. The reaction is conducted preferably at a temperature in the range of about 50° C. to relfux of the solvent. The reaction is preferably carried out under nitrogen or argon. The resulting compound of formula IV is isolated by conventional methods, for example, by extraction or filtration, and is purified by recrystallization or chromatography.

Alternatively, a known aminoketone salt of formula IX may be condensed with the diketone of formula III in the absence of a reducing agent, either in the aforementioned solvent system or in an aqueous solvent buffered from about pH 3–5, but not above pH 7.

A compound of IV can be converted to a compound of V by a Mannich reaction with dimethylamine hydrochloride and formaldehyde. Generally, an excess of formaldehyde and dimethylamine hydrochloride are used. Any solvent which is conventionally used in Mannich reactions, such as a lower alkanol such as ethanol may be employed. When a lower alkanol is used as the solvent, a byproduct may be formed which corresponds to the compound of formula V except that an alkoxymethylene substituent is attached to the pyrrole nitrogen in place of hydrogen. If desired this byproduct can be converted to the desired compound of formula V by treatment with an acid such as 2N hydrochloric acid. The Mannich reaction is generally run under an inert atmosphere at the reflux temperature of the solvent. Other known procedures for running the Mannich reaction, for example with a low boiling solvent under pressure, or using a preformed methyleneimmonium salt are also acceptable.

A compound of formula V is reacted with a quaternizing reagent such as dimethyl sulfate, or an alkyl halide such as methyl iodide, or methyl chloride, or most preferably methyl bromide. When methyl bromide is used it is bubbled as a gas into the reaction mixture. The quaternizing reaction is conducted in an aprotic organic solvent such as methylene chloride, or more preferably, chloroform, with occasional cooling to keep the temperature of the reaction mixture near room temperature.

The resulting organic salt of formula VI may be isolated by filtration and purified by recrystallization if desired. The anion of formula VI, Y−, may be halide, methylsulfate or the like, depending upon the quaternizing reagent used in the preparation of the compound of formula VI. The salt of formula VI is then reacted with base to yield a methylene compound of formula VII. The base utilized is generally an aqueous base such as dilute sodium hydroxide, potassium hydroxide, or barium hydroxide. The resulting methylene compound is isolated by conventional methods such as filtration or extraction, and purified by recrystallization or chromatography.

A methylene compound of formula VII is reacted with an equimolar amount of compound of a piperidine compound of formula VIII, which is a known compound or can be prepared according to known methods, to yield a compound of formula I' that is a compound of formula I, wherein $R_1$ is hydrogen. The reaction is conducted in a lower alkanol, such as methanol, propanol or more preferably ethanol, at a temperature in the range of room temperature to the reflux temperature of the solvent, more preferably reflux temperature of the solvent for a period of about 1 to about 36 hours. The resulting compound of formula I' can be isolated by conventional means such as filtration or extraction, and purified by recrystallization or chromatography.

If desired a compound of formula I' may be converted by alkylation or acylation to a compound of formula I wherein $R_1$ is lower alkyl or acyl. In this step the anion of a compound of formula I' is formed by treatment with a strong base in an aprotic medium, such as sodium methylsulfinyl carbanion in dimethylsulfoxide, lithium diisopropylamide in tetrahydrofuran, or n-butyllithium in tetrahydrofuran. The anion is then treated with an alkyl or acyl halide to afford a compound of formula I, which is isolated by conventional means, for example, by extraction or filtration, and purified by recrystallization of chromatography. In this step, compounds of formula I wherein $R_1$ and $R_6$ are the same may be produced by using two equivalents of base and two equivalents of an alkylating or acylating agent.

As is pointed out above, compounds of formula VIII are known compounds or can be prepared according to known methods.

Exemplary of compound of formula VIII are:
1-phenyl-1,3,8-triazaspiro[4.5]-decan-4-one;
1-cyclohexyl-1,3,8-triazaspiro[4.5]-decan-4-one;
1-phenyl-2-methyl-1,3,8-triazaspiro[4.5]-decan-4-one;
1-butyl-1,3,8-triazaspiro[4.5]-decan-4-one; and
1-(4-chlorophenyl)-1,3,8-triazaspiro[4.5]-decan-4-one.

As is pointed out above, compounds of formula II are known compounds or can be prepared in accordance with known methods. More specifically, a compound of formula II wherein $R_2$ and $R_3$ together form a ring of 5 to 8 carbon atoms can be prepared by reacting a compound of formula X

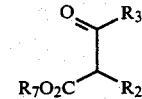

X wherein $R_2$ and $R_3$ are as described just above, and $R_7$ is methyl or ethyl with a strong base such as an aqueous alkali metal or alkaline earth metal hydroxide, preferably sodium hydroxide in water and sodium nitrite at a temperature in the range of about −20° C. to 5° C. preferably 0° C. The resulting compound of formula II can be separated by acidification followed by a conventional separatory technique such as extraction and purified by recrystallization.

Exemplary of compounds of formula II are:
2-hydroxyiminocyclopentanone;
2-hydroxyimino-3-pentanone;
2-hydroxyimino-2-butanone; and
2-hydroxyiminocyclopentanone.

The invention also relates to pharmaceutically acceptable acid addition salts of compounds of formula I. The compounds of formula I form acid additon salts with inorganic or organic acids. Thus, they form pharmaceutically acceptable acid addition salts with both pharmaceutically acceptable organic and inorganic acids, for example, with hydrohalic acid, such as, hydrochloric acid, hydrobromic acid, hydroiodic acid, and other mineral acid salts, such as sulfuric acid, nitric acid, phosphoric acid or the like, alkyl-and mono-aryl sulfonic acids, such as ethanesulfonic acid, toluene sulfonic acid, benzenesulfonic acid, or the like, other organic acids such as acetic acid, tartaric acid, maleic acid, oxalic acid, citric acid, benzoic acid, salicyclic acid, ascorbic acid and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt. The acid addition salt may also form hydrates.

The pharmaceutically acceptable salts produced are the functional equivalent of the corresponding compounds of formula I, and to the extent that salts of the invention are useful in therapy, the variety of salts encompasses by this invention are limited only by the criterion that the acids employed in forming the salts be pharmacologically and physiologically acceptable.

The compounds of formula I and their pharmaceutically acceptable acid addition salts are useful as anti-emetic agents. Compounds of formula I and their pharmaceutically acceptable acid addition salts exhibit useful pharmacological activity as dopamine receptor antagonists. Therefore they are especially useful as anti-emetic agents for the treatment of nausea and vomiting in mammals in need of such treatment. Compounds of formula I and their pharmaceutically acceptable acid addition salts also exhibit preferential action at peripheral receptor sites leading to a relative lack of central nervous system side effects, compared to known anti-emetic agents. Compounds of formula I and their pharmaceutically acceptable acid addition salts are also capable of blocking the emetic responses produced by a variety of chemical agents, including emetogenic cancer chemotherapeutic agents, such as cisplatin. These activites can be demonstrated in warm-blooded animals by the procedures described herein.

The spiroperidol binding test described below shows the activity of compounds of formula I in vitro in binding to dopamine receptors, which is a property of known anti-emetic agents.

SPIROPERIDOL BINDING TEST

Dopamine receptor antagonism by compounds of formula I in vitro is determined by the $^3$H-spiroperidol binding assay. In this test, rat striatal brain homogenates were incubated for 20 minutes in the presence of 0.2 nanomolar $^3$H-spiroperidol and varying concentrations of test compounds. The incubations were terminated by rapid filtrations through Whatman GF/B filters, followed by 2×5 mL washes with ice-cold assay buffer (50 mM tribase-HCl pH 7.7 which contains fixed concentrations of 0.1% ascorbic acid, 120 mM NaCl, 5 mM KCl, 2 mM CaCl$_2$, and 1 mM MgCl$_2$).

Compounds of Formula I exhibited activities as indicated in Table I. The IC$_{50}$ of a particular test compound is the concentration of test compound that inhibits the binding of spiroperidol to dopamine receptors by 50% as compared to the control.

TABLE 1

$^3$H—Spiroperidol Binding In Vitro for Compounds of Formula I

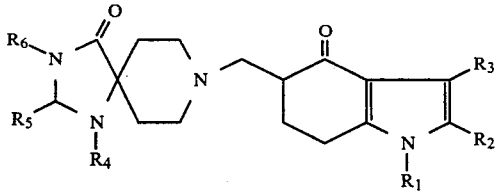

| Compd. | R$_1$ | R$_2$ | R$_3$ | R$_4$ | R$_5$ | R$_6$ | Binding IC$_{50}$, nM |
|---|---|---|---|---|---|---|---|
| Ia | H | CH$_3$ | CH$_2$CH$_3$ | Phenyl | H | H | 0.095 |
| Ib | H | —CH$_2$CH$_2$CH$_2$— | | Phenyl | CH$_3$ | H | 0.94 |
| Ic | H | —CH$_2$CH$_2$CH$_2$— | | Cyclohexyl | H | H | 0.52 |
| Id | H | CH$_3$ | CH$_3$ | Phenyl | H | H | 0.078 |
| Ie | H | CH$_3$ | CH$_2$CH$_3$ | Cyclohexyl | H | H | 0.082 |
| If | H | —CH$_2$CH$_2$CH$_2$— | | Phenyl | H | H | 0.35 |

As illustrated in Table I, compounds of formulas Ia-If are all potent dopamine receptor antagonist in vitro.

Further test data demonstrates the anti-emetic activity of compounds of formula I. More specifically, the further test data described below is in animals. The test descriptions and results are as follows:

ANTI-APOMORPHINE AND ANTI-D-AMPHETAMINE TESTS IN MICE

In species capable of emesis, apomorphine is a powerful emetic by virtue of its dopamine agonist activity at the chemoreceptor trigger zone. The ability of the dopamine antagonist neuroleptics to block apomorphine-induced emesis in dogs correlates with their human anti-emetic activity, and such compounds are clinically effective anti-emetics. Because classical neuroleptics block dopamine receptors both at the chemoreceptor trigger zone and within the central nervous system, a high incidence of central nervous system side effects are associated with their use as anti-emetics. Since the chemoreceptor trigger zone is functionally outside the blood-brain barrier, a dopamine receptor antagonist with anti-emetic activity which does not penetrate the central nervous system will not have central nervous system side effect liability. Compounds of formula I exhibit preferential action at receptors outside the blood-brain barrier, and show a wide separation between anti-emetic activity and central nervous system side effects.

Mice, unlike either dogs or humans, are incapable of emesis. However, mice respond to apomorphine by a well-characterized rearing response. This apomorphine-induced rearing in mice is analogous to an emetic response in a sensitive species, reflecting receptor occupancy in the mouse at a site analogous to the chemoreceptor trigger zone in animals which are capable of emesis. Blockade of D-amphetamine hyperactivity reflects blockade of central nervous system dopamine receptors. Therefore, an effective anti-emetic with a low central nervous system side effect liability should block apomorphine-induced rearing at lower doses than it blocks D-amphetamine hyperactivity. The procedures for the determination of anti-apomorphine rearing and anti-amphetamine hyperactivity in mice as follows:

PROCEDURE

The determination of anti-apomorphine of anti-D-amphetamine activities were carried out in fasted male CF-1 mice (47–54 days old) obtained from Charles River Inc., Kingston, NY.

Except as noted, anti-apomorphine rearing activity was determined two hours following the oral administration of the test compound, or at varying time intervals following at intravenous administration of the test compound. One mg/kg of apomorphine was administered intravenously using distilled water as the vehicle. The mice were then placed in individual wire mesh cages (3.5"×3.5"×3"). During the five to ten minute period following apomorphine administration the mice were observed for rearing (standing with the front legs against the side or top of the cage with the head arched back). Mice which reared fewer than three times during this period were considered to be protected from apomorphine.

Anti-D-amphetamine activity was determined as follows: groups of three mice per cage were housed in a plastic shoe box type cage (11.5"×7.5"×5") for approximately 24 hours prior to testing. The test compound was administered orally or intravenously to 6 mice per dose level and the vehicle was given to 12 mice. Immediately following dosing the mice were returned to their original cages from which the bedding has been removed. The cages were then placed on Stoelting Electronic (SE) Activity meters. At time intervals of one hour for orally administered test compounds, or at varying intervals for intravenously administered test compounds, the test compound-treated mice and six of the vehicle-treated mice received 10 mg/kg of D-amphetamine sulfate orally. The remaining six vehicle-treated mice received the vehicle for D-amphetamine sulphate, distilled water, orally. A constant dosage volume of 0.2 ml/kg was used. After dosing the mice were returned to their original cages and motor activity was monitored during the ten to seventy minutes after the dose period. A total of six activity meters were used simultaneously. Each meter held 2 sets of 3 mice each which comprised the mice of a given dose level, the vehicle-D-amphetamine sulphate group or the vehicle-vehicle group. The percent inhibition of hyperactivity was calculated using the vehicle-D-amphetamine activity level as measured on the SE Activity meter as 0% inhibition and the vehicle-vehicle activity level as measured on the SE Activity meter as 100% inhibition.

The $ED_{50}$ for apomorphine rearing is that dosage at which 50% of the mice treated were protected from apomorphine. Where an $ED_{50}$ dose was not determined, the percentage of animals protected from apomorphine rearing at an intravenous dose of 10 mg/kg was determined. The $ED_{50}$ for D-amphetamine hyperactivity is that dosage at which mice so treated had 50% inhibition of hyperactivity.

The results for compounds of formula I in the apomorphine rearing and D-amphetamine hyperactivity tests with the compounds of formula I being administered orally are set forth in Table II below. The test results in Table II, illustrate that compounds of formulas Id-Ie are active by the oral route of administration as antagonists of apomorphine rearing, and exhibit weak central nervous system activity in the amphetamine antagonism test. Thus, compounds of formulas Id-Ie exhibit an activity profile which indicates they would be useful as anti-emetic agents by the oral route of administration.

TABLE II

Antagonism of Apomorphine Rearing and Amphetamine Hyperactivity for Compounds of Formula I and Reference Compounds given by Oral Administration

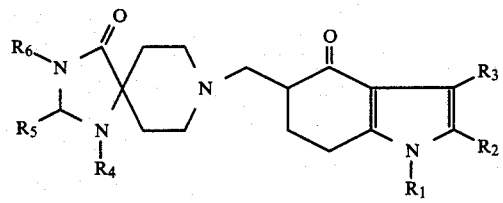

| Compd. | $R_1$ | $R_2$ | $R_3$ | $R_4$ | $R_5$ | $R_6$ | Antagonism of Apomorphine rearing[a] $ED_{50}$, mg/kg | Antagonism of Amphetamine Hyperactivity[a] $ED_{50}$, mg/kg |
|---|---|---|---|---|---|---|---|---|
| Ia | H | $CH_3$ | $CH_2CH_3$ | Phenyl | H | H | >100 po | >100 po |
| Ib | H | —$CH_2CH_2CH_2$— | | Phenyl | $CH_3$ | H | >100 po | >100 po |
| Ic | H | —$CH_2CH_2CH_2$— | | Cyclohexyl | H | H | >100 po | >100 po |
| Id | H | $CH_3$ | $CH_3$ | Phenyl | H | H | 12.0 po | 147.0 po |
| Ie | H | $CH_3$ | $CH_2CH_3$ | Cyclohexyl | H | H | 98.0 po | 235.0 po |
| If | H | —$CH_2CH_2CH_2$— | | Phenyl | H | H | 12.0 po | >100 po |
| Reference Compounds | | | | | | | | |
| chloropromazine HCl | | | | | | | 4.9 po | 2.1 po |
| haloperidol | | | | | | | 0.18 po | 0.23 po |
| domperidone | | | | | | | 23.0 po | 194.0 po |

[a]$ED_{50}$ values given in mg/kg for dosages given orally (po).

Results for compounds of formula I in the apomorphine rearing and D-amphetamine hyperactivity tests, wherein the compound of formula I was administered intravenously are set forth in Table III below. The test results in Table III, illustrate that compounds of formula Ia-Ie are active by the intravenous route of administration as antagonists of apomorphine rearing, and where tested, exhibit weak central nervous system activity in the amphetamine antagonism test. Thus, compounds of formula Ia-Ie exhibit an activity profile which indicates they would be useful as anti-emetic agents by the intravenous route of administration.

duced any grossly observable alteration in behavior or motor coordination nor were any other abnormal signs seen.

TABLE III

Antagonism of Apomorphine Rearing and D—Amphetamine Hyperactivity for Compounds of Formula I by Intravenous Administration

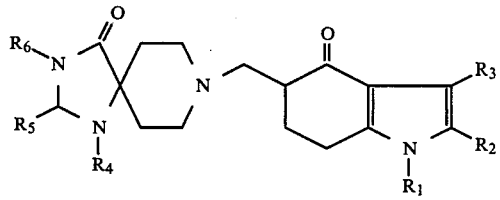

| Compd. | $R_1$ | $R_2$ | $R_3$ | $R_4$ | $R_5$ | $R_6$ | time$^a$ (hr) | Antagonism of Apomorphine Rearing ED$_{50}$ (mg/kg) | % protected at 10 mg/kg (%) | time$^a$ (hr) | Antagonism of Amphetamine Hyperactivity ED$_{50}$ (mg/kg) |
|---|---|---|---|---|---|---|---|---|---|---|---|
| Ia | H | CH$_3$ | CH$_2$CH$_3$ | Phenyl | H | H | 2 | 7.0 | — | 2 | 15.9 |
|    |   |       |              |        |   |   | 7 | 2.3 | — | 7 | 8.6 |
| Ib | H | —CH$_2$CH$_2$CH$_2$— | | Phenyl | CH$_3$ | H | 4 | — | 36 | — | — |
|    |   |                     | |        |        |   | 7 | — | 36 | — | — |
| Ic | H | —CH$_2$CH$_2$CH$_2$— | | Cyclohexyl | H | H | 4 | — | 40 | — | — |
|    |   |                     | |            |   |   | 7 | — | 40 | — | — |
| Id | H | CH$_3$ | CH$_3$ | Phenyl | H | H | 4 | 5.1 | — | 4 | >20 |
| Ie | H | CH$_3$ | CH$_2$CH$_3$ | Cyclohexyl | H | H | 4 | — | 62 | — | — |
|    |   |       |              |            |   |   | 7 | — | 79 | — | — |

$^a$Time after administration of the compound of formula I

Additional testing of the compound of formula If of the invention in anti-emetic tests is described just below:

ANTI-APOMORPHINE EMESIS IN DOGS

Pure-bred female Beagle dogs (Fa. WIGA, Versuchstier-Zuchtanstalt, 8741 Sulzfeld, GFR) with an approximate body weight of 15 kg were used. All dogs were shown previously to vomit at least four times during the 60 minutes following injection of 0.1 mg/kg apomorphine .HCl s.c. into the neck. Each dog was used in 14 day intervals. Three drug sessions were followed by an apomorphine control session.

The compound of formula If was administered suspended in 5% acacia at different dose levels by oral gavage to at least 4 dogs per dose. One hour later 0.1 mg/kg apomorphine .HCl was injected s.c. and the dogs observed for a further hour for vomiting. The anti-emetic effect was determined as the proportion of animals at a given dose level which did not vomit during the 1 hour observation period. For example, the ED$_{50}$ is the dose at which 50% of the animals at a given dose level did not vomit during the 1 hour observation period.

The compound of formula If had an anti-emetic ED$_{50}$ in this test of 0.75 mg/kg orally. The reference compound domperidone, a known anti-emetic, had an ED$_{50}$ of 0.2 mg/kg orally in the same test.

SIDE EFFECT EVALUATION IN DOGS

For side effect liability evaluation, pure breed beagle dogs from Marshall Inc., North Rose, N.Y., were used. Prior to dosing, the dogs were fasted for approximately 18 hrs. Dosing was orally by gelatin capsule. Following dosing, the dogs were observed for abnormal signs at 15 and 30 minutes, and 1,2,3,4,5, and 6 hours. Compound of formula Ia was initially administered orally at a dose of 1 mg/kg and then one day later at an oral dose of 10 mg/kg. An experienced observer monitored these dogs for six hours, following dosing. Neither dose level pro-

ANTI-CISPLATIN EMESIS IN DOGS

The anti-emetic activity of the compound of formula If was further demonstrated by demonstrating its activity in blocking cisplatin emesis in dogs. The procedure was as follows:

In the evaluation 6 male and 6 female Beagle dogs, supplied by White Eagle Laboratories, Doylestown PA., were used. Three dogs were tested daily. Each dog received either saline-placebo, 30 ml i.v.; the compound of formula If, 10 mg/kg i.v.; or domperidone 10 mg/kg i.v. The compound of formula If was dissolved in warm sterile water for injection. Domperidone was solubilized in acetic acid and the pH was adjusted with 2N NaOH. Both drugs were diluted to an infusion volume of 30 mL with sterile water. The treatments were infused over a 30-minute (n=3) or a 60-minute (n=9) period. Fifteen minutes after treatment, Platinol ® (cisplatin for injection, Bristol Laboratories) 3 mg/kg i.v., was administered and emetic activity was observed for 6 hours. The cisplatin, 1 mg/ml dissolved in sterile water, was infused over a 10 minute period. Each treatment was given to 2 male and 2 female weight-matched dogs.

The dogs were fed Wayne dog food moistened in water, 20 grams/kg, one hour prior to treatment. During the observation period the onset, frequency and severity of vomiting episodes as well as any atypical behavioral activity was recorded.

Statistical evaluation of emetic activity was done using Student's-t test for unpaired data.

As illustrated in Table IV, significant (ca.66%) inhibition of emesis compared to controls was observed with the compound of formula If. By contrast, domperidone did not differ significantly from controls. Thus the compound of formula If differs from domperidone in that the compound of formula If is effective against both apomorphine and cisplatin emesis in dogs, whereas domperidone is only effective against apomorphine emesis in dogs.

TABLE IV

CISPLATIN-INDUCED EMESIS IN FOUR BEAGLE DOGS

| TREATMENT | DOSE i.v. | VOMITING EPISODES Mean (± S.E.) 6 Hrs | VOMITING EPISODES Mean (± S.E.) 1 hr. |
|---|---|---|---|
| Saline (Cisplatin only) | 30 ml | 19.8 ± 6.5 | 3.3 ± 1.0 |
| Compound If | 10 mg/kg | 6.0 ± 1.8** | 1.0 ± 0.4* |
| Domperidone | 10 mg/kg | 12.5 ± 2.3 | 2.1 ± 0.7 |

*p ≦ 0.05 compared to cisplatin by the student's unpaired t-test.
**p ≦ 0.01 compared to cisplatin by the Mann-Whitney test.
p ≦ 0.057 compared to domperidone.

A compound of formula I or a pharmaceutically acceptable acid addition salt thereof can be administered by methods well known in the art. Thus, a compound of formula I or a pharmaceutically acceptable salt thereof can be administered either singly or with other pharmaceutical agents, for example, chemotherapeutic agents for cancer, orally, parenterally, or rectally. For oral administration a compound of formula I can be administered in the form of tablets, capsules, for example in admixture with talc, starch, milk, sugar, or other ingredients, that is pharmaceutically acceptable carriers, or in the form of aqueous solutions, suspensions, elixirs or aqueous alkanolic solutions, for example in admixture with sugar and other sweetening agents, flavoring agents, colorings, thickeners and other pharmaceutically acceptable excipients. For parenteral administration, a compound of formula I can be administered in solutions or suspensions, for example, as an aqueous or peanut oil solution or suspension using excipients and carriers conventional for this mode of administration.

From the above it can be seen that the invention relates to pharmaceutical compositions comprising a compound of formula I and a pharmaceutically acceptable carrier material.

In the practice of the invention, the dose of a compound of formula I or a pharmaceutically acceptable acid addition salt thereof, will be dependent on the potency and duration of activity of the particular compound of formula I or salt to be administered and on the route of administration, as well as the severity of the condition, age of the mammal to be treated and the like. Doses of a compound of formula I or pharmaceutically acceptable acid addition salts thereof, contemplated for use in practicing the invention are in the range of from about 0.35 mg/kg to about 20 mg/kg per day, preferably about 0.75 mg/kg to about 10 mg/kg per day either as a single dose or in divided doses.

The examples which follow further illustrate the invention. All temperatures are in degree Celsius unless otherwise stated.

EXAMPLE 1

Preparation of 1,2-Cyclopentanedione-2-Oxime

A mixture of ethyl 2-oxocyclopentanecarboxylate (93.6 g, 0.60 mol) and sodium hydroxide (26.4 g, 0.66 mol) in water (550 mL) was stirred in an ice bath during the addition of a solution of sodium nitrite (45.5 g 0.66 mol) in water (150 mL). After the addition, the cloudy mixture was stirred at room temperature for 48 hours until it became clear. The mixture was acidified to pH 5 with 20% HCl and extracted with dichloromethane (5×300 mL). The aqueous phase was concentrated in vacuo to abiout ⅓ the original volume and extracted again with dichloromethane (2×100 mL). The combined extracts were washed with brine, dried ($Na_2SO_4$), and concentrated to give the title compound as a low melting solid (44.4 g). A portion was recrystallized from petroleum ether to give crystalline title compound mp 68°–70° C.; IR ($CHCl_3$) 3580, 3280 (OH), 1744 (C=O), 1640 cm$^{-1}$ (C=N); NMR ($CDCl_3$ 206 (m, 2, $CH_2$), 2.50 (t, 2, J=7 Hz, $CH_2$), 2.84 (t, 2, J=7 Hz), 9.1 (br s, 1, OH).

EXAMPLE 2

Preparation of Hexahydro-4H-Cyclopent[b]Indol-8(8H)-One

To a mechanically stirred solution of 1,2-cyclopentanedione-2-oxime (25.0 g, 0.22 mol) and 1,3-cyclohexanedione (25.0 g, 0.22 mol) in 70% acetic acid (250 mL) was added zinc dust (43.0 g, 0.66 g-atom) in about 5-g portions (moderately exothermic) over a 30 minute period. After the addition, the mixture was heated to reflux for 2 hours and was then cooled to room temperature. The solution was decanted from excess zinc and poured into ice water (250 mL). The mixture was extracted with dichloromethane (1×200 mL, 2×100 mL) and the combined extracts were washed with saturated sodium bicarbonate to neutrality, then washed with brine, and dried ($Na_2SO_4$). The solution was concentrated to about 174 the original volume, whereupon the title cyclopent[b]indolone (8.3 g) separated as a light tan solid: mp 236°–238° C. (recrystallized from ethyl acetate); IR (KBr) 3210 (NH), 1620 cm$^{-1}$ (C=O); NMR ($CDCl_3$) δ 2.07 (m, 2, $CH_2$), 2.30–2.90 (m, 10, $CH_2$), 10.17 (br s, 1, NH); MS m/e 175 (M$^+$). Anal. Calcd for $C_{11}H_{13}NO$: C, 75.40; H, 7.48; N, 7.99. Found: C, 75.36; H, 7.38; N, 7.84.

EXAMPLE 3

Preparation of 1,2,3,5,6,7-Hexahydro-7-(Dimethylaminomethyl)-4H-Cyclopent[b]Indol-8(8H)-One A mixture of hexahydro-4H-cyclopent[b]indol-8(8H)-one (7.0 g, 0.04 mol), dimethylamine hydrochloride (4.88 g, 0.06 mol), and paraformaldehyde (1.8 g, 0.06 mol) in ethanol (140 mL) was heated to reflux for 18 hours. The solvent was then removed and the residue was chromatographed on silica gel (dry column) eluting with the organic phase of a mixture prepared by shaking (by volume) 90 parts chloroform, 30 parts methanol, 10 parts water, and 6 parts acetic acid. The eluant fractions containing the product were pooled, washed with bicarbonate, washed with brine, dried ($Na_2SO_4$), and evaporated to give the title dimethylaminomethyl cyclopentindolone compound as a white solid (3.9 g): mp 164°–165° C. (recrystallized from ethanol); IR ($CHCl_3$) 3460, 3275 (NH) and 1620 cm$^{-1}$ (C=O); NMR ($CDCl_3$) 2.24 (s, 6, N($CH_3$)$_2$) and 8.56 (br s, 1, NH); MS m/e 232 (M+). The compound was converted with HCl in ethanol to the hydrochloride salt 5HCl: mp 207°–208° C. (recrystallized from ethanol). Anal. Calcd for $C_{14}H_{20}N_2O$ HCl: C, 62.56; H, 7.88; N, 10.42. Found: C, 62.14; H, 7.80; N, 10.30.

EXAMPLE 4

Preparation of 1,2,3,5,6,7-Hexahydro-7-Methylene-4H-Cyclopent[b]Indol-8(8H)-One

Methyl bromide was bubbled into a solution of the Mannich base 1,2,3,5,6,7,-hexahydro-7(dimethylaminomethyl) 4H-cyclopent[b]indol-8(8H)-one (4.1 g, 17.5 mmol) in chloroform (100 mL) with occasional cooling to keep the temperature below 20° C. until no further precipitate was formed (20 minutes). The white suspension was stirred for 20 minutes and filtered to afford 5.0 g of the methylbromide salt of the title compond. A 3.5-g portion of the quaternary salt (10.6 mmol) was dissolved in water (30 mL) and treated at 0°–5° C. with 2N sodium hydroxide (10.5 mL). The mixture was stirred for 30 minutes and the precipitate of the title compound was filtered off, washed with water, and recrystallized from ethanol to give the title compound (0.95 g) as a white solid: mp 214°–215° C.; IR (KBr) 3205, 3160 (NH), 1648 (C=O), 1587 cm$^{-1}$ (C=C); NMR (CDCl$_3$) δ 2.40–2.80 (m, 10, CH$_2$), 5.37 and 5.98 (2d, 2, =CH$_2$); 9.96 (br s, 1, NH); MS m/e 187 (M+). Anal. Calcd for C$_{12}$H$_{13}$NO: C, 76.98; H, 7.00; N, 7.48. Found: C, 76.70; H, 6.98; N, 7.45.

EXAMPLE 5

Preparation of 1,2,3,5,6,7,-Hexahydro-7-[(4-Oxo-1-Phenyl-1,3,8-Triazaspiro[4,5]Decan-8-Ylmethyl]-4H-Cyclopent[b]Indol-8(8H)-One A mixture of the end product from Example 4, (3.0 g, 16.0 mmol) and 1-phenyl-1,3,8-triazaspiro[4,5]-decan-4-one (3.7 g, 16.0 mmol) in ethanol (90 mL) was heated to reflux for 24 hours. The solvent was evaporated and the residue chromatographed on silica gel (dry column) eluting with the organic phase of a mixture prepared by shaking 90 parts CHCl$_3$, 30 parts CH$_3$OH, 10 parts H$_2$O, and 6 parts acetic acid. Fractions were washed with dilute NH$_4$OH, dried (Na$_2$SO$_4$) and evaporated. Crystallization of the chromatographed product from ethanol afforded 3.35 g of the title compound as a white solid: mp 212°–213° C.; IR (KBr) 3240 (NH, OH), 1713 (C=O), and 1628 cm$^{-1}$ (C=O); NMR (CDCl$_3$+DMSO) 1.50–3.10 (m, 21, CH$_2$), 4.68 (s, 2, CH$_2$), 6.70–7.40 (m, 5, arom), 7.70 (s, 1, NH), and 9.77 (s, 1, NH); MS m/e 244, 187. Anal. Calcd for C$_{25}$H$_{30}$N$_4$O$_2$: C, 71.74; H, 7.23; N, 13.39. Found: C, 71.49; H, 7.29; N, 13.18.

Treatment of the free base with ethanolic HCl afforded the hydrochloride salt of the title compound mp 252°–253° C. (dec.). Anal. Calcd for C$_{25}$H$_{30}$N$_4$O$_2$.HCl: C, 65.99; H, 6.87; N, 12.31; Cl, 7.79. Found: C, 65.60; H, 6.89; N, 12.18; Cl, 7.77.

EXAMPLE 6

Preparation of 1,2,3,5,6,7-Hexahydro-7-[substituted and other substituted piperidinomethylindolones Piperidinomethyl]-4H-Cyclopent[b]-Indol-8(8H)-One Derivatives General Procedure.

A mixture of equimolar amounts of a compound of formula VII and a substituted piperidine derivative of formula VIII below in ethanol was heated to reflux for 20–24 hours. The solvent was evaporated and the residue chromatographed on silica gel (dry column) eluting with the organic phase of a mixture prepared by shaking 90 parts CHCl$_3$, 30 parts CH$_3$OH, 10 parts H$_2$O, and 6 parts acetic acid. Fractions were washed with dilute NH$_4$OH, dried (Na$_2$SO$_4$), and evaporated. The residue was crystallized from ethanol to afford the desired substituted 1,2,3,5,6,7-hexahydro-7-[substituted piperidinylmethyl-4H-cyclopent[b]-indol-8(8H)-one derivates and other substituted piperidinomethylindolones.

Following the general procedure, the analogs listed below were prepared.

A. From 1.9 g of 3-ethyl-2-methyl-5-methylene-4,5,6,7-tetrahydro-1H-indol-4-one and 2.3 g of 1-phenyl-1,3,8-triazaspiro[4.5]-decan-4-one in ethanol there was obtained 1.5 g of 8-[(3-ethyl-4,5,6,7-tetrahydro-2-methyl-4-oxo-1H-indol-5-yl)methyl]-1-phenyl-1,3,8-triazaspiro[4.5]-decan-4-one, mp 205°–7° C.

B. From 1.7 g of the product of Example 4 and 2.23 g of 2-methyl-1-phenyl-1,3,8-triazaspiro[4.5]decan-4-one in ethanol there was obtained 1.3 of 8-[(1,2,3,4,5,6,7,8-octahydro-8-oxocyclopent[b]indol-7-yl)methyl]-2-methyl-1-phenyl-1,3,8-triazaspiro[4.5]-decan-4-one, mp 234°–6° C.

C. From 1.87 g of the product of Example 4 and 2.37 g of 1-cyclohexyl-1,3,8-triazaspiro[4.5]decan-4-one there was obtained 1.3 g of 8-[(1,2,3,4,5,6,7,8-octahydro-8-oxocyclopent[b]indol-7-ylmethyl]-1-cyclohexyl-1,3,8-triazaspiro[4.5]decan-4-one, mp 211°–4° C.

D. From 1.9 g of 3-ethyl-2-methyl-5-methylene-4,5,6,7-tetrahydro-1H-indol-4-one and 2.37 g of 1-cyclohexyl-1,3,8-triazaspiro[4.5]-decan-4-one there was obtained 2.0 g of 8-[(3-ethyl-4,5,6,7-tetrahydro-2-methyl-4-oxo-1H-indol-5-yl)methyl]-1-cyclohexyl-1,3,8-triazaspiro[4.5]decan-4-one, mp 217°–9° C.

E. From 1.75 g of 2,3-dimethyl-5-methylene-4,5,6,7-tetrahydro-1H-indol-4-one and 2.3 g of 1-phenyl-1,3,8-triazaspiro[4.5]decan-4-one there was obtained 1.14 g of 8-[4,5,6,7-tetrahydro-(2,3-dimethyl-4-oxo-1H-indol-5-yl)methyl]-1-phenyl-1,3,8-triazaspiro[4.5]decan-4-one, mp 220°–2° C.

EXAMPLE 7

Preparation of 2-Hydroxyiminocyclopentanone

In a 3-L flask equipped with a mechanical stirrer and argon inlet was placed a solution of 70.5 g (1.76 mole) sodium hydroxide pellets in 1.0 L of water. The solution was cooled in an ice bath, and 250 g (1.60 mole) of ethyl 2-cyclopentanone carboxylate was added in one portion. The mixture was stirred while a solution of 121.5 g (1.76 mole) of sodium nitrite in 0.6 L of water was added dropwise over about 20 minutes. After the addition, the ice bath was removed and the mixture was allowed to stir at room temperature for 4 days. At the end of this period, the mixture was extracted with 2×200 mL of ether. The aqueous layer was the acidified with about 0.9 L of 2N HCl until it reached pH 3. The mixture was then extracted with 3×300 mL of ether, saturated with sodium chloride, and extracted with a further 5×300 mL of ether. The combined extracted were dried over Na$_2$SO$_4$ and evaporated at 35° C. on a rotary evaporator to afford a total of 124.0 g (68.5%) of 2-hydroxyiminocyclopentanone as a pale yellow oil which crystallized on standing in the freezer. A sample, recrystallized from 30°–60° petroleum ether, had mp 68°–70° C.

EXAMPLE 8

Preparation of Hexahydro-4H-Cyclopent[b]Indol-8(8H)-One

To a solution of 27.6 g (0.25 mole) of 1,3-cyclohexanedione and 27.6 g (0.244 mole) of the crude 2-hydroxyiminocyclopentanone in 435 mL of 70% aqueous acetic acid was added 47.6 g (0.73 g-atom) of zinc powder in about 5 g portions. The reaction was exothermic, but did not reach reflux. The mixture was heated to 80°–85° C. under argon for 2 hours and poured into 1.3 L of ice water and extracted with 3×300 mL of methylene chloride. The methylene chloride extracts were washed to neutrality with 3×500 mL of saturated sodium bicarbonate solution, dried over $Na_2SO_4$, and concentrated on a rotary evaporator to 50° C.

After removal of about 75% of the solvent, the title cyclopent[b]indolone precipitated from the solution and was collected by filtration and rinsed with methylene chloride to afford 9.6 g (22.4%) of the title compound as an off-white solid. A sample, recrystallized from ethyl acetate, had mp 236°–238° C.

EXAMPLE 9

Preparation of 1,2,3,5,6,7-Hexahydro-7-[(Dimethylamino)Methyl]-4H-Cyclopent[b]Indol-8(8H)-One A solution of 14.0 g (0.08 mole) of cyclopent[b]indolone of Example 8, 9.96 g (0.12 mole) of dimethylamine hydrochloride and 7.2 g (0.24 mole) of paraformaldehyde in 280 mL of 2B ethanol was heated to reflux and stirred mechanically for 20 hours. The solvent was removed on a rotary evaporator at 35° C. The residue showed unreacted cyclopent[b]indolone of Example 8, the desired title compound and a third component, identified as an ethoxymethyl substituted compound by thin layer chromatography. The residue was chromatographed on silica gel (dry column) eluting with the lower phase of a mixture prepared by shaking 90 parts $CHCl_3$, 30 parts $CH_3OH$, 10 parts $H_2O$, and 6 parts acetic acid. Fractions containing starting the ketone and the ethoxymethyl substituted compound eluted first. The fractions containing the title compound were washed with 10% $NH_4OH$, dried over $Na_2SO_4$, and concentrated on a rotary evaporator to give 6.7 g (36%) of title compound as an off-white solid. A sample, recrystallized from ethanol, had mp 165°–166° C.

EXAMPLE 9a

Preparation of 1,2,3,5,6,7-Hexahydro-7-[(Dimethylamino)Methyl]-4H-Cyclopent[b]Indol-8(8H)-One Alternatively, the title compound may be produced by following the procedure of Example 9 through the step of evaporating the solvent on a rotary evaporator. The resulting reaction mixture may be treated with 2N HCl, followed by extraction of the unreacted cyclopent[b]indolone of Example 8 with methylene chloride. The acid solution may then be warmed followed by basification with 2N NaOH to precipitate the Mannich product which is the title compound.

EXAMPLE 10

Preparation of 1,2,3,5,6,7-Hexahydro-7-[(Dimethylamino)Methyl]-4H-Cyclopent[b]Indol-8(8H)-One, Methylbromide Salt A solution of 20.7 g (0.089 mole) of the title compound of Example 9 in 300 mL of chloroform was cooled in an ice bath and methyl bromide gas was bubbled in for 30 minutes. After no further precipitate could be seen to form, the mixture was allowed to stir for 1 hour at 0° C. and was filtered. The solid methylbromide salt was dried at 25° C./1.0 mm overnight to give 27.2 g (93.3%) the title compound as a white solid.

EXAMPLE 11

Preparation of 1,2,3,5,6,7-Hexahydro-7-Methylene-4H-Cyclopent[b]Indol-8(8H)-One To a mechanically stirred suspension of 27.2 g (0.83 mole) of crude salt the title compound of Example 10 in 375 mL of water in an ice bath was added 80 mL (1.6 mole) of 2N NaOH solution via a dropping funnel. After the addition was complete, the mixture was stirred for 1 hour in the ice bath and was filtered. The filter cake of the title compound was dissolved in 500 mL of 9:1 methylene chloride:methanol. The organic phase was dried over $Na_2SO_4$, concentrated to a yellow solid. The damp solid was dried at 25° C./1.0 mm to give 12.95 g (83.5%) of the title compound. A sample, recrystallized from ethanol, had mp 214°–215° C.

EXAMPLE 12

Preparation of 1,2,3,5,6,7-Hexahydro-7-[(4-Oxo-1-Phenyl-1,3,8-Triazaspiro[4,5]decan-8-yl)-Methyl]-4H-Cyclopent[b]Indol-8(8H)-One, Hydrochloride A mixture of 6.0 g (0.032 mole) of the title compound of Example 11 and 7.45 g (0.032 mole) of 1-phenyl-1,3,8-triazaspiro[4.5]decan-4-one in 150 mL of ethanol was heated to reflux under argon for 48 hours. The solvent was evaporated and the residue chromatographed on 500 g of silica gel (dry column) eluting with the lower phase of a mixture prepared by shaking 90 parts $CHCl_3$, 30 parts $CH_3OH$, 10 parts $H_2O$, and 6 parts acetic acid. The fractions containing free base of the title compound were concentrated at 35°–50° C. on a rotary evaporator. The residue was dissolved in 500 mL of methylene chloride and neutralized to pH 10–11 with ice cold 1:1 $NH_4OH:H_2O$. The layers were separated and the organic phase was dried over $Na_2SO_4$ and concentrated. The residual solid was washed with hot ethanol and filtered. A sample of the free base, recrystallized from ethanol, had mp 183°–185° C. For the preparation of the HCl salt, the filter cake was suspended in 100 mL of ethanol and treated with about 10 mL of 5N HCl in ether. The solution was concentrated and allowed to cool, whereupon the hydrochloride salt of the title compound precipitated out. Two crops were collected, affording a total of 5.85 g of the hydrochloride salt of the title compound after drying at 100° C./1.0 mm overnight.

In the examples of formulations, the compounds are as follows:

Compund If is 1,2,3,5,6,7-hexahydro-7-[(4-oxo-1-phenyl-1,3,8-triazaspiro[4.5]decan-8-yl)methyl]-4H-cyclopent[b]indol-8(8H)-one.

Compound Ia is 8-[(3-ethyl-4,5,6,7-tetrahydro-2-methyl-4-oxo-1H-indol-5-yl)methyl]-1-phenyl-1,3,8-triazaspiro[4.5]-decan-4-one.

Compound Ib is 8-[(1,2,3,4,5,6,7,8-octahydro-8-oxocyclopent[b]indol-7-yl)methyl]-2-methyl-1-phenyl-1,3,8-triazaspiro[4.5]-decan-4-one.

Compound Ic is 8-[(1,2,3,4,5,6,7,8-octahydro-8-oxocyclopent[b]indol-7-yl)methyl]-1-cyclohexyl-1,3,8-triazaspiro[4.5]-decan-4-one.

Compound Id is 8-[4,5,6,7-tetrahydro-(2,3-dimethyl-4-oxo-1H-indol-5-yl)methyl]-1-phenyl-1,3,8-triazaspiro[4.5]decan-4-one.

Compound Ie is 8-[(3-ethyl-4,5,6,7-tetrahydro-(2-methyl-4-oxo-1H-indol-5-yl)methyl]-1-cyclohexyl-1,3,8-triazaspiro[4.5]decan-4-one.

EXAMPLE 13

| | PARENTERAL FORMULATION (for intravenous and intramuscular use) | | |
|---|---|---|---|
| ITEM | INGREDIENTS | MG/ML | |
| 1. | Compound If* | 2.0 mg | 10.0 mg |
| 2. | Propylene glycol** | 100 mg | 500 mg** |
| 3. | Emulphor** | 10 mg | 50 mg* |
| 4. | Water for Injection q.s. to | 1 ml | 1 ml |

Method for Preparation:

(1) Dissolve items 2 and 3 in water for injection
(2) Add item 1 and dissolve or suspend into the solution from Step 1
(3) Adjust the pH using dilute sodium hydroxide or hydrochloric Acid.***
(4) Add water for injection to the acquired amount.
(5) Fill the solution into a suitable container.

*Formulation may also be applied to compounds of formulas Ia,Ib,Ic,Id, and Ie.
**Solvents or solubilizers such as polyethylene glycol, alcohol, dimethylacetamide, glycerine, povidone, lecithin, sorbitan monooleate and trioleate, Polysorbate 20 or 80 may be used in combination or alone to achieve adequate solubility and stabilization.
***Buffers such as citrate, acetate or phosphate may be incorporated for adequate stabilization.

EXAMPLE 14

| | TABLET FORMULATION (Dry Granulation) | | |
|---|---|---|---|
| ITEM | INGREDIENTS | MG/tablet | |
| 1. | Compound If* | 2 mg | 20 ml |
| 2. | Starch | 20 mg | 40 mg |
| 3. | Avicel | 40 mg | 80 mg |
| 4. | Lactose | 137 mg | 274 mg |
| 5. | Magnesium sterate | 1 mg | 2 mg |
| | | 200 mg | 400 mg |

Method for Preparation:

1. Mix items 3 and 4 in a suitable blender.
2. Add and mix the compound of formula If to the mixture from Step 1.
3. Add and mix item 2 to the mixture from Step 2.
4. Add and mix item 5 to the mixture from Step 3.
5. Compress the granulation on a suitable tablet press.

*Formulation may also be applied to Compounds of formulas Ia,Ib,Ic,Id, and Ie.

We claim:

1. A compound of the formula

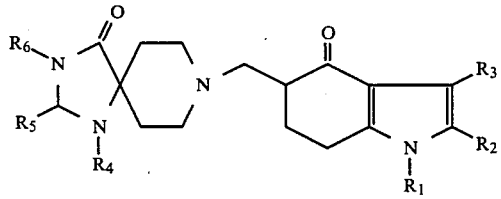

wherein $R_1$ is hydrogen, lower alkyl or acyl; $R_2$ and $R_3$ independently are lower alkyl, alkyl substituted by phenyl, or alkyl substituted by phenyl bearing one or more substituents selected from the group consisting of halogen, trifluoromethyl, lower alkyl, lower alkoxy, nitro, amino, lower alkylamino and di-lower alkylamino or a straight or branched chain unsaturated hydrocarbon containing 2 to 7 carbon atoms or $R_2$ and $R_3$ together are trimethylene or tetramethylene; $R_4$ is phenyl; phenyl bearing one or more substituents selected from the group consisting of chlorine, fluorine, bromine, iodine, hydroxy and lower alkyl, cyclohexyl, cyclohexyl bearing one or more substituents selected from the group consisting of chlorine, fluorine, bromine, iodine, hydroxy and lower alkyl, cyclopentyl, cyclopentyl bearing one or more substituents selected from the group consisting of chlorine, fluorine, bromine, iodine, hydroxy and lower alkyl, cycloheptyl, or cycloheptyl bearing one or more substituents selected from the group consisting of chlorine, fluorine, bromine, iodine, hydroxy and lower alkyl; $R_5$ is hydrogen, or lower alkyl, $R_6$ is hydrogen, lower alkyl; or acyl; or a pharmaceutically acceptable acid addition salt thereof.

2. A compound in accordance with claim 1, wherein $R_5$ and $R_6$ each is hydrogen.

3. A compound in accordance with claim 2 wherein $R_2$ and $R_3$ together are trimethylene and $R_4$ is phenyl.

4. A compound in accordance with claim 3, 1,2,3,5,6,7-hexahydro-7-[(4-oxo-1-phenyl-1,3,8-triazaspiro[4.5]decan-8yl)methyl]-4H-cyclopent[b]indol-8(8H)-one, or a pharmaceutically acceptable acid addition salt thereof.

5. A compound in accordance with claim 2, 8-[(3-ethyl-4,5,6,7-tetrahydro-2-methyl-4-oxo-1H-indol-5-yl)methyl]-1-phenyl-1,3,8-triazaspiro[4.5]-decan-4-one or a pharmaceutically acceptable acid addition salt thereof.

6. A compound in accordance with claim 2, 8-[4,5,6,7-tetrahydro-(2,3-dimethyl-4-oxo-1H-indol)-5-yl)methyl]-1-phenyl-1,3,8-triazaspiro[4.5]-decan-4-one, or a pharmaceutically acceptable acid addition salt thereof.

7. A pharmaceutical composition for inducing an anti-emetic effect comprising an anti-emetically effective amount of a compound of the formula

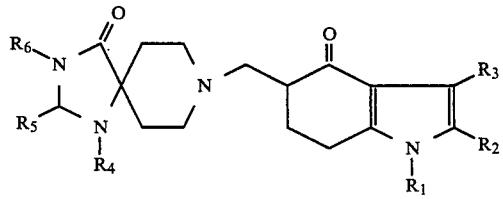

wherein $R_1$ is hydrogen, lower alkyl or acyl; $R_2$ and $R_3$ independently are lower alkyl, alkyl substituted by phenyl, or alkyl substituted by phenyl bearing one or more substituents selected from the group consisting of halogen, trifluoromethyl, lower alkyl, lower alkoxy, nitro, amino, lower alkylamino and di-lower alkylamino or a straight or branched chain unsaturated hydrocarbon containing 2 to 7 carbon atoms or $R_2$ and $R_3$ together are trimethylene or tetramethylene; $R_4$ is phenyl; phenyl bearing one or more substituents selected from the group consisting of chlorine, fluorine, bromine, iodine, hydroxy and lower alkyl, cyclohexyl, cyclohexyl bearing one or more substituents selected from the group consisting of chlorine, fluorine, bromine, iodine, hydroxy and lower alkyl, cyclopentyl, cyclopentyl bearing one or more substituents selected from the group consisting of chlorine, fluorine, bromine, iodine, hydroxy and lower alkyl, cycloheptyl, or cycloheptyl bearing one or more substituents selected from the group consisting of chlorine, fluorine, bromine, iodine, hydroxy and lower alkyl; $R_5$ is hydrogen, or lower alkyl, $R_6$ is hydrogen, lower alkyl; or acyl; or a pharmaceutically acceptable acid addition salt thereof; and a pharmaceutically acceptable carrier material.

8. A composition in accordance with claim 7 wherein $R_5$ and $R_6$ each is hydrogen, $R_2$ and $R_3$ together are trimethylene and $R_4$ is phenyl.

9. A composition in accordance with claim 8 wherein the compound of formula I is 1,2,3,5,6,7-hexahydro-7-[(4-oxo-1-phenyl-1,3,8-triazaspiro[4.5]decan-8-yl)methyl]-4H-cyclopent[b]indol-8(8H)-one, or a pharmaceutically acceptable acid addition salt thereof.

10. A method of inducing an anti-emetic effect which comprises administering to a mammal requiring such treatment an anti-emetically effective amount of a compound of the formula

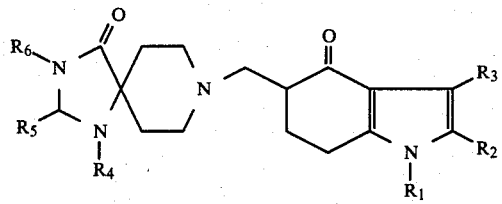

wherein $R_1$ is hydrogen, lower alkyl or acyl; $R_2$ and $R_3$ independently are lower alkyl, alkyl substituted by phenyl, or alkyl substituted by phenyl bearing one or more substituents selected from the group consisting of halogen, trifluoromethyl, lower alkyl, lower alkoxy, nitro, amino, lower alkylamino and di-lower alkylamino or a straight or branched chain unsaturated hydrocarbon containing 2 to 7 carbon atoms or $R_2$ and $R_3$ together are trimethylene or tetramethylene; $R_4$ is phenyl; phenyl bearing one or more substituents selected from the group consisting of chlorine, fluorine, bromine, iodine, hydroxy and lower alkyl, cyclohexyl, cyclohexyl bearing one or more substituents selected from the group consisting of chlorine, fluorine, bromine, iodine, hydroxy and lower alkyl, cyclopentyl bearing one or more substituents selected from the group consisting of chlorine, fluorine, bromine, iodine, hydroxy and lower alkyl, cyclopentyl, cycloheptyl, or cycloheptyl bearing one or more substituents selected from the group consisting of chlorine, fluorine, bromine, iodine, hydroxy and lower alkyl; $R_5$ is hydrogen, or lower alkyl; and $R_6$ is hydrogen, lower alkyl; or acyl; or a pharmaceutically acceptable acid addition salt thereof.

11. A method in accordance with claim 10, wherein $R_5$ and $R_6$ each is hydrogen; $R_2$ and $R_3$ together are trimethylene and $R_4$ is phenyl.

12. A method in accordance with claim 11, wherein the compound of formula I is 1,2,3,5,6,7-hexahydro-7-[(4-oxo-1-phenyl-1,3,8-triazaspiro[4.5]decan-8-yl)methyl]-4H-cyclopent[b]indol-8(8H)-one, or a pharmaceutically acceptable acid addition salt thereof.

* * * * *